United States Patent [19]

Joseph et al.

[11] Patent Number: 5,238,733
[45] Date of Patent: Aug. 24, 1993

[54] STRETCHABLE NONWOVEN WEBS BASED ON MULTI-LAYER BLOWN MICROFIBERS

[75] Inventors: Eugene G. Joseph, Arden Hills; Leigh E. Wood, Woodbury, both of Minn.; Dennis L. Krueger, Hudson, Wis.; Paul R. Suszko, Hastings; Daniel E. Meyer, Stillwater, both of Minn.

[73] Assignee: Minnesota Mining and Manufacturing Company, St. Paul, Minn.

[21] Appl. No.: 768,173

[22] Filed: Sep. 30, 1991

[51] Int. Cl.$^5$ ............................................. B32B 27/00
[52] U.S. Cl. ....................... 428/284; 156/167; 428/288; 428/297; 428/298; 428/343; 428/369; 428/373; 428/903; 428/910
[58] Field of Search ............... 428/297, 298, 903, 284, 428/288, 369, 910, 343, 373; 156/167

[56] References Cited

U.S. PATENT DOCUMENTS

| | | | |
|---|---|---|---|
| 3,480,502 | 11/1969 | Schrenk | 156/271 |
| 3,487,505 | 1/1970 | Chisholm et al. | 18/13 |
| 3,557,265 | 1/1971 | Chisholm et al. | 264/47 |
| 3,672,802 | 6/1972 | Matsui et al. | 425/131 |
| 3,681,189 | 8/1972 | Matsui et al. | 161/175 |
| 3,687,589 | 8/1972 | Schrenk | 425/109 |
| 3,759,647 | 9/1973 | Schrenk et al. | 425/131 |
| 3,825,379 | 7/1974 | Lohkamp et al. | 425/72 |
| 3,841,953 | 10/1974 | Lohkamp et al. | 161/150 |
| 3,849,241 | 11/1974 | Butin et al. | 161/169 |
| 3,924,990 | 12/1975 | Schrenk | 425/131 |
| 4,048,364 | 9/1977 | Harding et al. | 428/113 |
| 4,103,058 | 7/1978 | Humlicek | 428/171 |
| 4,117,194 | 9/1978 | Barbe et al. | 428/374 |
| 4,118,531 | 10/1978 | Hauser | 428/224 |
| 4,197,069 | 4/1980 | Cloeren | 425/131.1 |
| 4,295,809 | 10/1981 | Mikami et al. | 425/72 S |
| 4,323,534 | 4/1982 | DesMarais | 264/176 R |
| 4,375,718 | 3/1983 | Wadsworth et al. | 29/592 E |
| 4,381,274 | 4/1983 | Kessler et al. | 264/147 |
| 4,427,737 | 1/1984 | Cilento et al. | 428/315.7 |
| 4,429,001 | 1/1984 | Kolpin et al. | 428/283 |
| 4,460,649 | 7/1984 | Park et al. | 428/373 |
| 4,477,516 | 10/1984 | Sugihara et al. | 428/296 |
| 4,557,972 | 12/1985 | Okamoto et al. | 428/373 |
| 4,627,950 | 12/1986 | Matsui et al. | 264/103 |
| 4,652,487 | 3/1987 | Morman | 428/138 |
| 4,710,190 | 12/1987 | Wood et al. | 604/389 |
| 4,724,184 | 2/1988 | Killian et al. | 428/227 |
| 4,729,371 | 3/1988 | Krueger et al. | 128/206.19 |
| 4,741,944 | 5/1988 | Jackson et al. | 428/903 |
| 4,755,178 | 7/1988 | Insley et al. | 604/367 |
| 4,818,463 | 4/1989 | Buehning | 264/40.1 |
| 4,929,492 | 5/1990 | Carey, Jr. et al. | 428/198 |
| 4,939,008 | 7/1990 | Komaki | 428/34.3 |
| 4,986,743 | 1/1991 | Buehning | 425/7 |

FOREIGN PATENT DOCUMENTS

| | | |
|---|---|---|
| 0341875 | 11/1989 | European Pat. Off. |
| 0366379 | 2/1990 | European Pat. Off. |
| 0432489A2 | 6/1991 | European Pat. Off. |
| WO/90/03464 | 4/1990 | PCT Int'l Appl. |

OTHER PUBLICATIONS

Wente, Van A., "Superfine Thermoplastic Fibers", *Industrial Engineering Chemistry*, vol. 48, pp. 1342-1346.

Wente, Van A. et al., "Manufacture of Superfine Organic Fibers", Report No. 4364 of the Naval Research Laboratories, published May 25, 1954.

*Primary Examiner*—James J. Bell
*Attorney, Agent, or Firm*—Gary L. Griswold; Roger R. Tamte; William J. Bond

[57] ABSTRACT

A highly conformable and deformable nonwoven web comprising melt-blown microfibers having multiple layers of a relatively low modulus material and a high modulus material.

30 Claims, 4 Drawing Sheets

STRETCHABLE NONWOVEN WEBS BASED ON MULTI-LAYER BLOWN MICROFIBERS

FIELD OF THE INVENTION

The invention relates to a conformable or stretchable novel melt-blown non-woven web useful in a variety of applications and the method for its production. The nonwoven webs include melt-blown microfibers comprised of longitudinally distinct polymeric layers of at least one elastomeric or low modulus material and a second higher modulus or nonelastomeric material.

BACKGROUND OF THE INVENTION

It has been proposed in U.S. Pat. No. 3,841,953 to form nonwoven webs of melt-blown fibers using polymer blends, in order to obtain webs having novel properties. A problem with these webs however is that the polymer interfaces causes weaknesses in the individual fibers that causes severe fiber breakage and weak points. The web tensile properties reported in this patent are generally inferior to those of webs made of corresponding single polymer fibers. This web weakness is likely due to weak points in the web from incompatible polymer blends and the extremely short fibers in the web.

A method for producing bicomponent fibers in a melt-blown process is disclosed in U.S. Pat. No. 4,729,371. The polymeric materials are fed from two conduits which meet at a 180 degree angle. The polymer flowstreams then converge and exit via a third conduit at a 90 degree angle to the two feed conduits. The two feedstreams form a layered flowstream in this third conduit, which bilayered flowstream is fed to a row of side-by-side orifices in a melt-blowing die. The bi-layered polymer melt streams extruded from the orifices are then formed into microfibers by a high air velocity attenuation or a "melt-blown" process. The product formed is used specifically to form a web useful for molding into a filter material. The process disclosed concerns forming two-layer microfibers. The process also has no ability to produce webs where web properties are adjusted by fine control over the fiber layering arrangements and/or the number of layers. There is also not disclosed a stretchable and preferably high strength web.

U.S. Pat. No. 4,559,972 discloses a sheath-core composite fiber of an allegedly ultrafine denier (less than 0.5 denier). The fibers are formed from a special spinneret for forming large, three-component fibers, with two of the components forming ultrafine included material in a matrix of the third component. Ultrafine fibers are then obtained by selectively removing the matrix (the "sea") material, leaving the included material as fine fibers. This process is complex and cannot practically be used to form non-woven webs. Similar processes are proposed by U.S. Pat. Nos. 4,460,649, 4,627,950 and 4,381,274, which discuss various "islands-in-a-sea" processes for forming multi-component yarns. U.S. Pat. No. 4,117,194 describes a bicomponent textile spun fiber with improved crimp properties.

U.S. Pat. Nos. 3,672,802 and 3,681,189 describe spun fibers allegedly having a large number of layers each of a separate polymer component. The two polymers are fed into a specially designed manifold that repeatedly combines, splits and re-combines a polymer stream(s) to form a somewhat stratified stream of the two distinct polymers. The process disclosed in these two patents is similar to mixing the polymers due to the significant amount of non-linear polymer flow introduced during the repeated splitting and re-combining of the polymer stream(s). However, the splitting and re-combining is done in line with the polymer flow, and the resulting fibers apparently have distinct longitudinal regions of one or the other polymer rather than the substantially non-directional arrangement of separate polymer regions one would obtain with incomplete batch mixing. However, the polymer layers in the fibers are very indistinct and irregular. Further, due to the excessively long contact period between the polymers, it would be difficult to handle polymers with significantly different melt viscosities by this process. The fibers produced are textile size, and the layering effect is done to improve certain properties over homogeneous fibers (not webs) such as dyeability properties, electrification properties, hydrophilic properties or tensile properties. No mention is made of how to improve web conformability and/or stretchability.

SUMMARY OF THE INVENTION

The present invention is directed to a process for producing a non-woven web of longitudinally layered melt-blown microfibers and the nonwoven, melt-blown web, comprising layers of a low modulus or elastomeric materials and adjacent layers of higher modulus or non-elastic materials. The microfibers are produced by a process comprising first feeding separate polymer melt streams to a manifold means, optionally separating at least one of the polymer melt streams into at least two distinct streams, and combining all the melt streams, including the separated streams, into a single polymer melt stream of longitudinally distinct layers, preferably of the at least two different polymeric materials arrayed in an alternating manner. The combined melt stream is then extruded through fine orifices and formed into a highly conformable and stretchable web of melt-blown microfibers.

DESCRIPTION OF THE PREFERRED EMBODIMENTS

Figure 1:
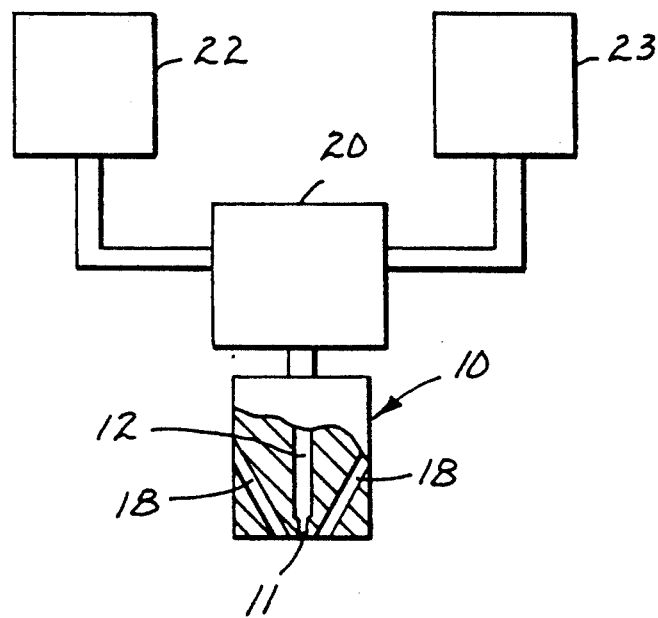
FIG. 1 is a schematic view of an apparatus useful in the practice of the invention method.

The microfibers produced are prepared, in part, using the apparatus discussed, for example, in Wente, Van A., "Superfine Thermoplastic Fibers," *Industrial Engineering Chemistry*, Vol. 48, pp 1342–1346 and in Wente, Van A. et al., "Manufacture of Superfine Organic Fibers," Report No. 4364 of the Naval Research Laboratories, published May 25, 1954, and U S. Pat. Nos. 3,849,241 (Butin et al.), 3,825,379 (Lohkamp et al.), 4,818,463 (Buehning), 4,986,743 (Buehning), 4,295,809 (Mikami et al.) or 4,375,718 (Wadsworth et al.). These apparatuses and methods are useful in the invention process in the portion shown as die 10 in FIG. 1, which could be of any of these conventional designs.

The polymeric components are introduced into the die cavity 12 of die 10 from a separate splitter, splitter region or combining manifold 20, and into the, e.g., splitter from extruders, such as 22 and 23. Gear pumps and/or purgeblocks can also be used to finely control the polymer flowrate. In the splitter or combining manifold 20, the separate polymeric component flowstreams are formed into a single layered flowstream. However, preferably, the separate flowstreams are kept out of direct contact for as long a period as possible prior to reaching the die 10. The separate polymeric flowstreams from the extruder(s) can be split in the splitter (20). The split or separate flowstreams are combined only immediately prior to reaching the die, or die orifices. This minimizes the possibility of flow instabilities generating in the separate flowstreams after being combined in the single layered flowstream, which tends to result in non-uniform and discontinuous longitudinal layers in the multi-layered microfibers. Flow instabilities can also have adverse effects on non-woven web properties such as strength, temperature stability, or other desirable properties obtainable with the invention process.

The separate flowstreams are also preferably established into laminar flowstreams along closely parallel flowpaths. The flowstreams are then preferably combined so that at the point of combination, the individual flows are laminar, and the flowpaths are substantially parallel to each other and the flowpath of the resultant combined layered flowstream. This again minimizes turbulence and lateral flow instabilities of the separate flowstreams in and after the combining process. It has been found that a suitable splitter 20, for the above-described step of combining separate flowstreams, is one such as is disclosed, for example, in U.S. Pat. No. 3,557,265, which describes a manifold that forms two or three polymeric components into a multi-layered rectilinear melt flow. The polymer flowstreams from separate extruders are fed into plenums then to one of the three available series of ports or orifices, each series of ports is in fluid communication with one of the plenums. Each stream is thus split into a plurality of separated flowstreams by one of the series of ports, each with a height-to-width ratio of from about 0.01 to 1. The separated flowstreams, from each of the three plenum chambers, are, then simultaneously coextruded by the three series of parts into a single channel in an interlacing manner to provide a multi-layered flowstream. The combined, multi-layered flowstream in the channel is then transformed (e.g., in a coat hanger transition piece), so that each layer extruded from the manifold orifices has a substantially smaller height-to-width ratio to provide a layered combined flowstream at the die orifices with an overall height of about 50 mils or less, preferably 15-30 mils or less. The width of the flowstream can be varied depending on the width of the die. Other suitable devices for providing a multi-layer flowstream are such as disclosed in U.S. Pat. Nos. 3,924,990 (Schrenk); 3,687,589 (Schrenk); 3,759,647 (Schrenk et al.) or 4,197,069 (Cloeren), all of which, except Cloeren, disclose manifolds for bringing together diverse polymeric flowstreams into a single, multi-layer flowstream that is ordinarily sent through a coat hanger transition piece or neck-down zone prior to the film die outlet. The Cloeren arrangement has separate flow channels in the die cavity. Each flow channel is provided with a back-pressure cavity and a flow-restriction cavity, in successive order, each preferably defined by an adjustable vane. The adjustable vane arrangement permits minute adjustments of the relative layer thicknesses in the combined multi-layered flowstream. The multilayer polymer flowstream from this arrangement need not necessarily be transformed to the appropriate length/width ratio, as this can be done by the vanes, and the combined flowstream can be fed directly into the die cavity 12.

The multi-layer polymer flowstream is normally fed into the die cavity 12 as an integral flow. However, it is possible to keep the layer flowstreams separate in the die cavity 12 by use of separator plates that would allow the separate polymer flowstreams to combine immediately prior to reaching the die orifices.

From the die cavity 12, the multi-layer polymer flowstream is extruded through an array of side-by-side orifices 11. As discussed above, prior to this extrusion, the feed can be formed into the appropriate profile in the cavity 12, suitably by use of a conventional coat hanger transition piece. Air slots 18, or the like, are disposed on either side of the row of orifices 11 for directing uniform heated air at high velocity at the extruded layered melt streams. The air temperature is generally about that of the meltstream, although preferably 20°-30° C. higher than the polymer melt temperature. This hot, high-velocity air draws out and attenuates the extruded polymeric material, which will generally solidify after traveling a relatively short distance from the die 10. The solidified or partially solidified fibers are then formed into a web by known methods and collected (not shown). The collecting surface can be a solid or perforated surface in the form of a flat surface or a drum, a moving belt, or the like. If a perforated surface is used, the backside of the collecting surface can be exposed to a vacuum or low-pressure region to assist in the deposition of fibers, such as is disclosed in U.S. Pat. No. 4,103,058 (Humlicek). This low-pressure region allows one to form webs with pillowed low-density regions. The collector distance can generally be from 3 to 50 inches from the die face. With closer placement of the collector, the fibers are collected when they have more velocity and are more likely to have residual tackiness from incomplete cooling. This is particularly true for inherently more tacky thermoplastic materials, such as thermoplastic elastomeric materials. Moving the collector closer to the die face, e.g., preferably 3 to 12 inches, will result in stronger inter-fiber bonding and a less lofty web. Moving the collector back will generally tend to yield a loftier and less coherent web.

The temperature of the polymers in the splitter region is generally about the temperature of the higher melting point component as it exits its extruder. This splitter region or manifold is typically integral with the die and is kept at the same temperature. The temperature of the separate polymer flowstreams can also be controlled to bring the polymers closer to a more suitable relative viscosity. When the separate polymer flowstreams converge, they should generally have an apparent viscosity of from 150 to 800 poise (measured by a capillary rheometer). The relative viscosities of the separate polymeric flowstreams to be converged should generally be fairly well matched. Empirically, this can be determined by varying the temperature of the melt and observing the crossweb properties of the collected web. The more uniform the crossweb properties, the better the viscosity match. The overall viscosity of the layered combined polymeric flowstream(s) at the die face should be from 150 to 800 poise, preferably from 200 to 400 poise. The differences in relative viscosities are preferably generally the same as when the separate polymeric flowstreams are first combined. The apparent viscosities of the polymeric flowstream(s) can be adjusted at this point by varying the temperatures as per U.S. Pat. No. 3,849,241 (Butin, et al).

The size of the polymeric fibers formed depends to a large extent on the velocity and temperature of the attenuating airstream, the orifice diameter, the temperature of the melt stream, and the overall flow rate per orifice. At high air volume rates, the fibers formed have an average fiber diameter of less than about 10 micrometers. However, there is an increased difficulty in obtaining webs having uniform properties as the air flow rate increases. At more moderate air flow rates, the polymers have larger average diameters, however, with an increasing tendency for the fibers to entwine into formations called "ropes". This is dependent on the polymer flow rates, of course, with polymer flow rates in the range of 0.05 to 0.5 gm/min/orifice generally being suitable. Coarser fibers, e.g., up to 25 micrometers or more, can be used in certain circumstances such as large pore, or coarse, filter webs.

The multi-layer microfibers of the invention can be admixed with other fibers or particulates prior to being collected. For example, sorbent particulate matter or fibers can be incorporated into the coherent web of blown multi-layered fibers as discussed in U.S. Pat. Nos. 3,971,373 or 4,429,001. In these patents, two separate streams of melt-blown fibers are established with the streams intersecting prior to collection of the fibers. The particulates, or fibers, are entrained into an airstream, and this particulate-laden airstream is then directed at the intersection point of the two microfiber streams. Other methods of incorporating particulates or fibers, such as staple fibers, bulking fibers or binding fibers, can be used with the invention melt-blown microfiber webs, such as is disclosed, for example, in U.S. Pat. Nos. 4,118,531, 4,429,001 or 4,755,178, where particles or fibers are delivered into a single stream of melt-blown fibers.

Other materials such as surfactants or binders can be incorporated into the web before, during or after its collection, such as by use of a spray jet. If applied before collection, the material is sprayed on the stream of microfibers, with or without added fibers or particles, traveling to the collection surface.

The microfibers are formed from a low modulus material forming one layer or layers and a relatively nonelastic material forming the other layer or layers.

Low modulus material refers to any material that is capable of substantial elongation, e.g. preferably greater than about 100 percent, without breakage. At low stress levels, the Young's modulus is generally in the range from about $10^4$ to $10^7$ N/M$^2$. These materials are preferably elastomers which will substantially resume their shape after being stretched. Such elastomers will preferably exhibit permanent set of about 20 percent or less, preferably 10 percent or less, when stretched at moderate elongations, preferably of about 100 percent. Elastomers include materials or blends, which are capable of undergoing elongations, preferably of up to 700–800% and more at room temperatures.

The relatively nonelastic material is generally a more rigid or higher modulus material capable of being coextruded with the elastomeric or low modulus material. Further, the relatively nonelastic material must undergo permanent deformation or cold stretch at the stretch percentage that the elastomeric or low modulus material will undergo without significant elastic recovery. The Young's modulus of this material should generally be greater than $10^6$ N/M$^2$ and preferably greater than $10^7$ N/M$^2$.

Webs formed from these multilayer fibers exhibit remarkable conformability, which is believed due to the extensibility of individual fibers in a coherent web structure under low levels of stress. Webs also exhibit a remarkable extensibility without the usual web breakage. This is believed to be attributable to a unique complimentary combination of properties from the individual layers in the multilayer fibers and from the interfiber relationships in the web as a whole. The preferably elastomeric low modulus layers allows one to lower the individual fiber composite modulus to a level that permits ready extensibility at relatively low stress levels. As such, when the web is tensioned, the applied stress will dissipate by elongation of individual fibers rather than concentrating at web weak points, which could result in fiber breakage and web failure.

Fiber breakage of the individual fibers that undergo elongation is believed to be minimized by the relatively nonelastic material. As discussed above, preferably the relatively nonelastic material is one that will undergo permanent deformation when stretched. Such materials also exhibit significant orientation when stretched, and their modulus value and strength tends to significantly increase at some point as they are stretched. Therefore, the relatively nonelastic material layers act as reinforcing elements at a critical elongation point. As adjacent unextended, or less extended, portions of the web are still relatively extensible, fully extended and oriented fibers are unlikely to be exposed to stress levels high enough to cause fiber and web breakage. It is believed that the layers of low modulus material act to distribute the stress while the layers of higher modulus material reinforce critically stressed portions of web thus decreasing the tendency for fiber and web failure. The stress on the web therefore has a tendency to be more widely distributed across the entire web rather than resulting in failure at web weak points.

Further, when the low modulus material is an elastomer it will have a tendency to resume its original shape after being elongated. This thus results in a tendency for the web to contract after being stretched. This web contraction has been found to vary significantly depending on the materials used in the elastomer layer and the higher modulus layer, the relative volume percent of the respective layers and the overall number of layers in the microfibers. Generally the most recovery is exhibited by webs formed of microfibers having a relatively low number of layers and a higher volume percent of the elastomeric layer material. The individual fibers that exhibit recovery also are self-crimping. Namely, the fibers tend to coil and recover into a springlike form. The web after recovery will generally exhibit elastic properties to the point of previous elongation. This can range from levels as low as a few percent to a greater than 100 or 200 percent.

Fiber coiling and occasional separation of individual outer layers from stressed fibers also results in a relatively high degree of lofting in the resultant web. This lofting yields an improved softness or feel to the web, making it desirable for use in applications where it may make skin contact such as bandage backings, garment elastics, surgical drapes, medical tape backings or medical wraps. With respect to garments, particular contemplated uses include uses in a disposable diaper or incontinent device as any elastic element, or a conformable body hugging portion such as an outer or inner cover sheet or a portion designed to engage the hips of the wearer, for a product designed to be stepped into or slipped on.

In certain embodiments, the elastic recovery of stretched webs can be enhanced by heating the web. This heat-activated recovery can be used to advantage to create a heat-shrink elastic nonwoven web product for use in a wide variety of applications, particularly when this is coupled with the conformable nature of the web.

When used as a tape backing, the nonwoven web can be coated with any conventional hot melt, solvent coated, or like adhesive suitable for application to nonwoven webs. These adhesives can be applied by conventional techniques, such as solvent coating by methods such as reverse roll, knife-over-roll, gravure, wire wound rod, floating knife or air knife, hot-melt coating such as; by slot orifice coaters, roll coaters or extrusion coaters, at appropriate coating weights. The extensible nature of the web can have considerable effects on a previously applied adhesive layer. When the web is stretched, the adhesive layer, if continuous, will break up resulting in a breathable tape. Further, the amount of adhesive surface available for contact to a substrate will likely be significantly reduced. The tape could thus be used for single application purposes and be rendered nonfunctional when removed (as the web tape backing could be designed to yield when removed) if the adhesion is reduced to an appropriate level. This would make the tape well suited for certain tamper indicating uses as well as with products designed for single use only. Adhesives can also be applied after the web has been extended or stretched. Preferred for most applications would be pressure sensitive adhesives.

The low modulus material can be any such material suitable for processing by melt blowing techniques. This would include polymers such as polyurethanes (e.g. "Morthane TM", available from Morton Thiokol Corp.); A-B block copolymers where A is formed of poly(vinyl arene) moieties such as polystyrene, and B is an elastomeric mid-block such as a conjugated diene or a lower alkene in the form of a linear di- or tri-block copolymer, a star, radial or branched copolymer, such as elastomers sold as "KRATON TM" (Shell Chemical Co.); polyetheresters (such as "Arnitel" available from Akzo Plastics Co.); or polyamides (such as "Pebax TM" available from Autochem Co.). Copolymers and blends can also be used. For example, A—B block copolymer blends as described in U.S. Pat. No. 4,657,802 are suitable where such block copolymers are preferably blended with polyalkylenes. Other possible materials include ethylene copolymers such as ethylene vinyl acetates, ethylene/propylene copolymer elastomers or ethylene/propylene/diene terpolymer elastomers. Blends of all the above materials are also contemplated provided that the resulting material has a Young's modulus of approximately $10^7$ N/M$^2$ or less, preferably $10^6$ N/M$^2$ or less.

For extremely low modulus elastomers, it may be desirable to provide greater rigidity and strength. For example, up to 50 weight percent, but preferably less than 30 weight percent, of the polymer blend can be stiffening aids such as polyvinylstyrenes, polystyrenes such as poly(alpha-methyl)styrene, polyesters, epoxies, polyolefins, e.g., polyethylene or certain ethylene/vinyl acetates, preferably those of higher molecular weight, or coumarone-indene resin.

Viscosity reducing materials and plasticizers can also be blended with the elastomers and low modulus extensible materials such as low molecular weight polyethylene and polypropylene polymers and copolymers, or tackifying resins such as Wingtack TM aliphatic hydrocarbon tackifiers available from Goodyear Chemical Company. Tackifiers can also be used to increase the adhesiveness of an elastomeric low modulus layer to a relatively nonelastic layer. Examples of tackifiers include aliphatic or aromatic liquid tackifiers, polyterpene resin tackifiers, and hydrogenated tackifying resins. Aliphatic hydrocarbon resins are preferred.

The relatively nonelastomeric layer material is a material capable of elongation and permanent deformation as discussed above, which is fiber forming. Useful materials include polyesters, such as polyethylene terephthalate; polyalkylenes, such as polyethylene or polypropylene; polyamides, such as nylons; polystyrenes; or polyarylsulfones. Also useful are certain slightly elastomeric materials such as some olefinic elastomeric materials such as some ethylene/propylene, or ethylene/propylene/diene elastomeric copolymers or other ethylenic copolymers such as some ethylene vinyl acetates.

The relatively non-elastomeric layer material can also be a material capable of heat or sonic bonding to itself or other materials. A preferred material is disclosed in U.S. Pat. No. 4,710,190, the substance of which is incorporated by reference, which describes a blend of high and low molecular weight portion polymers. The blends of high and low molecular weight portions are blends that exhibit tackiness and bonding characteristics at temperatures in the range of 50° C. to 110° C. The high and low molecular weight portions can include ethylene- or propylene-based copolymers. Particularly preferred are copolymers with polar comonomers such as ethylene/vinyl acetate (EVA), or like materials (see, e.g., E.P.A. 366379 A2). Also usable are blends of EVA and tackifiers such as synthetic hydrocarbon resins. These materials exhibit good bonding to polyethylene-based polymers or copolymer films such as polyethylene or EVA films. Although not as preferred, other heat- or sonic-bondable materials can be used as the relatively non-elastomeric layer, however, it is preferred that this material have a melting point at least about 15° C. below that of the elastomeric layer so that the web retains some open structure following heat bonding. Suitable materials would include polyethylene polymers and blends such as disclosed in U S. Pat. No. 4,477,516.

Heat or sonicly bondable materials often exhibit relatively high self-bonding characteristics under melt-blowing conditions and, as such, form very coherent webs without the elastomeric (or low modulus) material. Webs formed from these combinations of materials can be concentricly layered (e.g., sheath-core-type layering) with the heat sealable or sonicly sealable material as the external sheath layer and exhibit some of the properties of the longitudinally layered embodiments.

The combination of an elastomeric layer (as a core layer or the like) and an outer bonding layer provides elastomeric and/or conformable webs capable of heat or sonic bonding to structures such as polyethylene polymer or copolymer films or webs. This finds particular use where properties of conformability, elasticity and breathability are important, and where the web could be heat or sonicly bonded to other components of a device, such as medical devices or incontinent devices (e.g., a diaper film or the like).

A property of the invention web when stretched and allowed to recover is the directionality of the resulting web's elasticity. The web will exhibit elastic properties substantially only in the direction the web is stretched. The elasticity is also limited by the point to which the web was originally stretched. The elastic behavior and loft of the web can thus be controlled to an appropriate level, depending on the application. For example, for bandage backings, a limited level of elasticity is all that is required. This desired level of elasticity could be obtained by adjusting the number of layers in the microfibers, the relative percent of the at least two layers (one of which is an elastomeric layer) or the degree or direction of elongation or stretch. A low degree (e.g., less than 50%) of elasticity is thus obtainable for uses such as medical wraps, bandages and the like. Higher degrees of elasticity (e.g, greater than 50%) are obtainable for uses such as the elastication of garments.

As previously discussed, the web when stretched also displays a noted lofting effect, which is dependant to some degree on the amount of recovery. This loft is highly desirable for garment and medical type uses. The increased loft will increase the web softness, breathability and wicking ability.

A further feature of the invention webs is an ability for the webs to undergo further recovery when heated generally to a temperature greater than about 60° C. This is useful for typical heat shrink applications for elastic films.

Fiber and web strength can be controlled within wide ranges for given combinations of polymers by varying, independently, the relative ratios of the polymers, the layer order in the microfibers, the number of layers, the collector distance and other process variables. The invention thus allows precise control of web strength by varying one or all of these variables.

Theoretically, for webs formed from the above described two types of layers either one can advantageously comprise 1 to 99 volume percent of the total fiber volume, however, preferably the low modulus material will comprise at least about 10 percent of the fiber volume. At the low end of this volume range, the outside layers will still contribute significantly to the surface properties of the fibers forming the web without significantly modifying the bulk fiber properties, such as tensile strength and modulus behavior. In this manner, the polymers with desirable bulk properties, such as tensile strength (e.g., the relative nonelastic materials), can be combined with materials having desirable surface properties, such as good bondability (e.g., an elastomeric low modulus material), to provide melt-blown webs with a high relative proportion of the desirable properties from each polymer. At higher percentages, the outer layers will still contribute disproportionately to fiber surface properties, but will contribute more to the fiber bulk properties.

With the invention, the web properties can also be altered by variations in the number of layers employed at a given relative volume percent and layer arrangement. As described above, variation in the number of layers, at least at a low number of layers, has a tendency to significantly vary the relative proportion of each polymer (assuming two polymeric materials) at the microfiber surface. This (assuming alternating layers of two polymeric materials) translates into variation of those web properties to which the microfiber surface properties significantly contribute. Thus, web properties can change depending on what polymer or composition comprises the outside layer(s). However, as the number of layers increases, this variation in web properties based on surface area effects diminishes. At higher-layer numbers, the relative thicknesses of the individual fiber layers will tend to decrease, significantly decreasing the surface area effect of any individual layer. For the preferred melt-blown microfibers with average diameters of less than 10 micrometers, the individual fiber layer thicknesses can get well below 1 micrometer.

Additional effects on the fiber and web properties can be attributed to increases in the number of fiber layers alone. Specifically, it has been found that web modulus increases with increases in the number of individual layers while the elastic recovery behavior of the stretched web goes down significantly. Although not wishing to be bound by theory, it is believed that the decrease in individual layer thicknesses in the microfiber has a significant effect on the crystalline structure and behavior of the component polymers. For example, spherulitic growth could be constrained by adjacent layers resulting in more fine-grained structures. Further, the interfacial layer boundaries may constrain transverse polymer flow in the orifice increasing the relative percent of axial flow, tending to increase the degree of order of the polymers in the layered form and hence could increase crystallinity in this manner. These factors can likely influence the macro scale behavior of the component fibers in the web and hence web behavior itself.

Further, with increased microfiber layering, the number of interfaces, and interfacial area, between adjacent layers increases significantly. This could tend to increase strength due to increased reinforcement and constrainment of the individual layers. It has also been found that it becomes increasingly difficult to separate the fiber inner layers as the total number of layers in the fibers increase. This is true even for relatively incompatible polymers that would ordinarily require compatibilizers or bonding layers to prevent layer separation.

The number of layers obtainable with the invention process is theoretically unlimited. Practically, the manufacture of a manifold, or the like, capable of splitting and/or combining multiple polymer streams into a very highly layered arrangement would be prohibitively complicated and expensive. Additionally, in order to obtain a flowstream of suitable dimensions for feeding to the die orifices, forming and then maintaining layering through a suitable transition piece can become difficult. A practical limit of 1,000 layers is contemplated, at which point the processing problems would likely outweigh any potential added property benefits.

The webs formed can be of any suitable thickness for the desired end use. However, generally a thickness from 0.01 to 5 centimeters is suitable for most applications. Further, for some applications, the web can be a layer in a composite multi-layer structure. The other layers can be supporting webs or films (such as elastic films, semi-permeable films or impermeable films). Other layers could be used for purposes such as absorbency, surface texture, rigidification and can be nonwoven webs formed of, for example, staple and/or melt-blown fibers. The other layers can be attached to the invention melt-blown web by conventional techniques such as heat bonding, binders or adhesives or mechanical engagement, such as hydroentanglement or needle punching. Other structures could also be included in a composite structure, such as reinforcing or elastic threads or strands, which would preferably be sandwiched between two layers of the composite structures. These strands or threads can likewise be attached by the conventional methods described above.

A particular contemplated use for the nonwoven web is as a tape backing capable of being firmly bonded to a substrate, and removed therefrom by stretching the backing at an angle less than about 35°. These tapes are useful as mounting and joining tapes (e.g., adhesive on both faces) or for removable labels or the like (adhesive on one face). The highly extensible backing (having a Young's modulus of less than 50,000 PSI and preferably between 5,000 and 30,000 PSI) deforms along a propagation front creating a concentration of stress at the propagation front. This stress concentration results in adhesive failure at the deformation propagation front at relatively low forces. The tape can thus be removed cleanly at low forces, without damage to the substrate, yet provide a strong bond in use. The adhesive for this application should generally be extensible, yet can otherwise be of conventional formulations such as tackified natural or synthetic rubber pressure sensitive adhesives or acrylic based adhesives. When applied, the tape should be unstretched or stretched to a low extent (e.g., to enhance conformability) so that the backing is still highly extensible (e.g., greater than 50%, and preferably greater than 150%).

Webs, or composite structures including webs of the invention, can be further processed after collection or assembly such as by calendaring or point embossing to increase web strength, provide a patterned surface, or fuse fibers at contact points in a web structure or the like; by orientation to provide increased web strength; by needle punching; heat or molding operations; coating, such as with adhesives to provide a tape structure, or the like.

The following examples are provided to illustrate presently contemplated preferred embodiments and the best mode for practicing the invention, but are not intended to be limiting thereof.

TEST PROCEDURES

Tensile Modulus

Tensile modulus data on the multi-layer BMF webs was obtained using an Instron Tensile Tester (Model 1122) with a 10.48 cm (2 in.) jaw gap and a crosshead speed of 25.4 cm/min. (10 in./min.). Web samples were 2.54 cm (1 in.) in width. Elastic recovery behavior of the webs was determined by stretching the sample to a predetermined elongation and measuring the length of the sample after release of the elongation force and allowing the sample to relax for a period of 1 minute.

Wide Anqle X-Ray Scattering Test

X-Ray diffraction data were collected using a Philips APD-3600 diffractometer (fitted with a Paur HTK temperature controller and hot stage). Copper K $\alpha$ radiation was employed with power tube settings of 45 kV and 4 mA and with intensity measurements made by means of a Scintillation detector. Scans within the 2–50 degree ($2\theta$) scattering region were performed for each sample at 25 degrees C. and a 0.02 degree step increment and 2 second counting time.

Conformability

Conformability was measured according to the manufacturer's directions on a Handle-o-Meter TM Model 211, available from Thwing-Albert Instrument Co. using an 8 in. $\times$ 8 in. (20.3 cm $\times$ 20.3 cm) sample using a $\frac{1}{4}$ in. (0.64 cm) slot width.

Thermal Properties

Melting and crystallization behavior of the polymeric components in the multi-layered BMF webs were studied using a Perkin-Elmer Model DSC-7 Differential Scanning Calorimeter equipped with a System 4 analyzer. Heating scans were carried out at 10° or 20° C. per minute with a holding time of three (3) minutes above the melting temperature followed by cooling at a rate of 10° C. per minute. Areas under the melting endotherm and the crystallization exotherm provided an indication of the amount of crystallinity in the polymeric components of the multi-layered BMF webs.

EXAMPLE 1

A polypropylene/polyurethane multi-layer BMF web of the present invention was prepared using a melt-blowing process similar to that described, for example, in Wente, Van A., "Superfine Thermoplastic Fibers," in *Industrial Engineering Chemistry*. Vol. 48, pages 1342 et seq (1956), or in Report No. 4364 of the Naval Research Laboratories, published May 25, 1954, entitled "Manufacture of Superfine Organic Fibers" by Wente, Van A.; Boone, C. D.; and Fluharty, E. L., except that the BMF apparatus utilized two extruders, each of which was equipped with a gear pump to control the polymer melt flow, each pump feeding a five-layer feedblock splitter assembly similar to that described in U.S. Pat. Nos. 3,480,502 (Chisholm et al.) and 3,487,505 (Schrenk) which was connected to a melt-blowing die having circular smooth surfaced orifices (10/cm) with a 5:1 length to diameter ratio. The first extruder (260° C.) delivered a melt stream of a 800 melt flow rate (MFR) polypropylene (PP) resin (PP 3495G, available from Exxon Chemical Corp.), to the feedblock assembly which was heated to about 260° C. The second extruder, which was maintained at about 220° C., delivered a melt stream of a poly(esterurethane) (PU) resin ("Morthane TM" PS 455-200, available from Morton Thiokol Corp.) to the feedblock. The feedblock split the two melt streams. The polymer melt streams were merged in an alternating fashion into a five-layer melt stream on exiting the feedblock, with the outer layers being the PP resin.

The gear pumps were adjusted so that a 75:25 pump ratio percent PP:PU polymer melt was delivered to the feedblock assembly and a 0.14 kg/hr/cm die width (0.8 lb/hr/in.) polymer throughput rate was maintained at the BMF die (260° C.). The primary air temperature was maintained at approximately 220° C. and at a pressure suitable to produce a uniform web with a 0.076 cm gap width. Webs were collected at a collector to BMF die distance of 30.5 cm (12 in.). The resulting BMF web, comprising five-layer microfibers having an average diameter of less than about 10 micrometers, had a basis weight of 50 g/m$^2$.

EXAMPLE 2

A BMF web having a basis weight of 50 g/m² and comprising five-layer microfibers having an average diameter of less than about 10 micrometers was prepared according to the procedure of Example 1, except that the PP and PU melt streams were delivered to the five-layer feedblock in a 50:50 ratio.

EXAMPLE 3

A BMF web having a basis weight of 50 g/m² and comprising five-layer microfibers having an average diameter of less than about 10 micrometers was prepared according to the procedure of Example 1, except that the PP and PU melt streams were delivered to the five-layer feedblock in a 25:75 ratio.

CONTROL WEB I

A control web of the 800 MFR polypropylene resin was prepared according to the procedure of Example 1, except that only one extruder, which was maintained at 260° C., was used, and it was connected directly to the BMF die through a gear pump. The die and air temperatures were maintained at 260° C. The resulting BMF web had a basis weight of 50 g/m² and an average fiber diameter of less than about 10 micrometers.

CONTROL WEB II

A control web of the polyurethane resin ("Morthane ™" PS455-200) was prepared according to the procedure of Example 1, except that only one extruder, which was maintained at 220° C., was used which was connected directly to the BMF die through a gear pump. The die and air temperatures were maintained at 220° C. The resulting BMF web had a basis weight of 50 g/m² and an average fiber diameter of less than about 10 micrometers.

Table 1 summarizes the tensile modulus values for BMF webs comprising five-layer microfibers of varying PP/PU polymer ratios.

TABLE 1

Tensile Modulus
Five-Layer PP/PU BMF Webs
50 g/m² Basis Weight

| Example | Pump Ratio PP/PU | Tensile Modulus MD kPa | XMD kPa |
|---|---|---|---|
| Control I | 100:0 | 2041 | 2897 |
| 1 | 75:25 | 6821 | 9235 |
| 2 | 50:50 | 8083 | 9490 |
| 3 | 25:75 | 8552 | 12214 |
| Control II | 0:100 | 1055 | 1814 |

EXAMPLE 4

Figure 6:
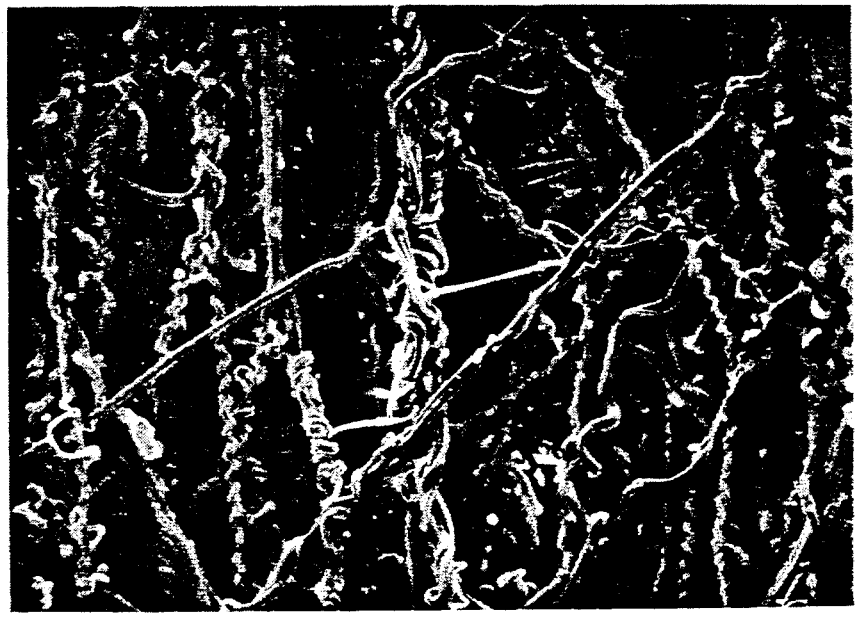
FIG. 6 is a scanning electron micrograph top view of an Example 4 web.

A BMF web having a basis weight of 100 g/m² and comprising two-layer microfibers having an average diameter of less than about 10 micrometers was prepared according to the procedure of Example 3, except that the PP and PU melt streams were delivered to a two-layer feedblock, and the die and air temperatures were maintained at about 230° C. This sample was stretched and released. This sample was then prepared for scanning electron micrograph analysis. FIG. 6 shows a top view of this stretched sample (200x). The machine direction conformability was 174 grams, and the cross direction conformability was 227 grams.

EXAMPLE 5

A BMF web having a basis weight of 100 g/m² and comprising three-layer microfibers having an average diameter of less than about 10 micrometers was prepared according to the procedure of Example 3, except that the PP and PU melt streams were delivered to a three-layer feedblock. The machine direction conformability was 188 grams, and the cross direction conformability was 277 grams.

EXAMPLE 6

A BMF web having a basis weight of 100 g/m² and comprising five-layer microfibers having an average diameter of less than about 10 micrometers was prepared according to the procedure of Example 3. Example 3 is a five-layer construction. The machine direction conformability was 185 grams, and the cross direction conformability was 252 grams.

EXAMPLE 7

A BMF web having a basis weight of 100 g/m² and comprising twenty-seven-layer microfibers having an average diameter of less than about 10 micrometers was prepared according to the procedure of Example 3, except that the PP and PU melt streams were delivered to a twenty-seven-layer feedblock. The machine direction conformability was 149 grams, and the cross direction conformability was 185 grams.

Table 2 summarizes the modulus values for a series of BMF webs having a 25:75 PP:PU pump ratio, but varying numbers of layers in the microfibers.

TABLE 2

Web Modulus as a Function of Layers in Microfiber
25:75 PP/PU Pump Ratio
100 g/m² Basis Weight

| Example | Number of Layers | MD Tensile Modulus (kPa) |
|---|---|---|
| 4 | 2 | 10835 |
| 5 | 3 | 11048 |
| 6 | 5 | 15014 |
| 7 | 27 | 17097 |

Figure 2:
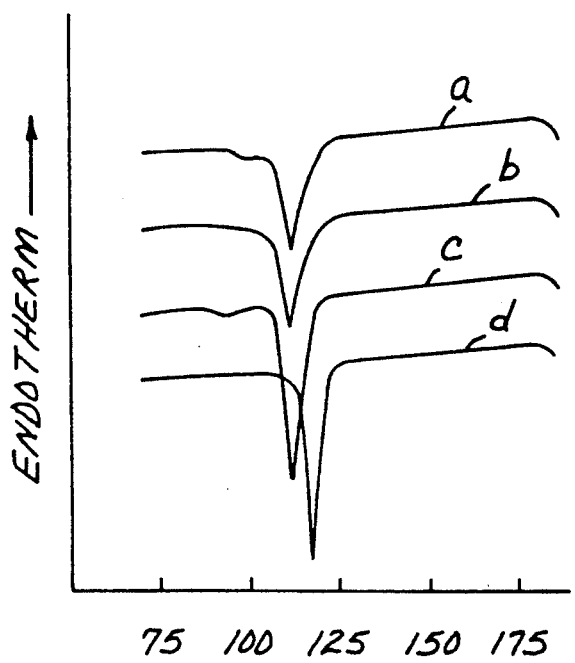
FIG. 2 is a plot of differential scanning calorimetry scans for Examples 4–7 showing increasing exotherms with increasing layering.
Figure 3:
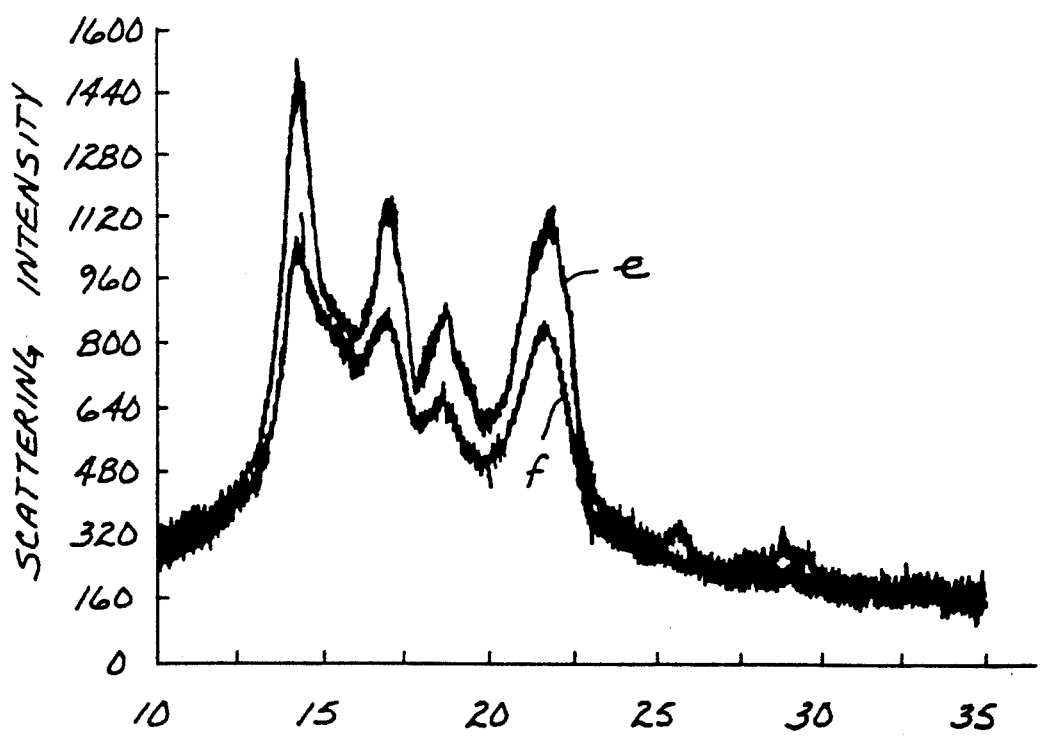
FIG. 3 is a plot of wide-angle x-ray scattering for Examples 5 and 7 showing increasing crystallinity with increasing layering.

The effect that the number of layers within the microfiber cross-section had on the crystallization behavior of the PP/PU BMF webs was studied using differential scanning calorimetry the results of which are graphically presented in FIG. 2. An examination of the crystallization exotherms for the BMF webs of Examples 4, 5, 6 and 7 (a, b, c and d, respectively), which corresponds to blown microfibers having 2, 3, 5 and 27 layers, respectively, indicates that the peak of the crystallization exotherm for the web of Example 7 is approximately 6° C. higher than the corresponding peak values for webs comprising blown microfibers having fewer layers. This data suggests that the crystallization process is enhanced in the microfibers having 27 layers, which is further supported by the examination of the wide angle X-ray scattering data that is illustrated in FIG. 3 and confirms higher crystallinity in the PP of the 27 layer microfiber web samples (e corresponds to Example 7 and f corresponds to Example 5 after washing out the PU with tetrahydrofuran solvent).

EXAMPLE 8

A BMF web having a basis weight of 100 g/m² and comprising two-layer microfibers having an average diameter of less than about 10 micrometers was prepared according to the procedure of Example 1, except that a 105 MI low-density polyethylene (LLDPE, Aspun TM 6806 available from Dow Chemical) was substituted for the polypropylene and a poly(esterurethane) (PU) resin ("Morthane TM " PS 440-200, available from Morton Thiokol Corp.) was substituted for the Morthane TM PS 455-200, the extruder temperatures were maintained at 220° C. and 230° C., respectively, the melt streams were delivered to a two-layer feedblock maintained at 230° C. at a 75:25 ratio, the BMF die and primary air supply temperatures were maintained at 225° C. and 215° C., respectively, and the collector distance was 30.5 cm. The machine direction conformability was 157 grams, and the cross direction conformability was 181 grams.

EXAMPLE 9

A BMF web having a basis weight of 100 g/m$^2$ and comprising two-layer microfibers having an average diameter of less than about 10 micrometers was prepared according to the procedure of Example 8, except that the PE and PU melt streams were delivered to the two-layer feedblock in a 50:50 ratio. The machine direction conformability was 115 grams, and the cross direction conformability was 150 grams.

EXAMPLE 10

A BMF web having a basis weight of 100 g/m$^2$ and comprising two-layer microfibers having an average diameter of less than about 10 micrometers was prepared according to the procedure of Example 8, except that the PE and PU melt streams were delivered to the two-layer feedblock in a 25:75 ratio. The machine direction conformability was 70 grams, and the cross direction conformability was 103 grams.

CONTROL WEB III

A control web of the LLDPE resin (Aspun TM 6806) was prepared according to the procedure of Example 1, except that only one extruder, which was maintained at 210° C., was used, and it was connected directly to the BMF die through a gear pump, and the die and air temperatures were maintained at 210° C., and the collector distance was 25.4 cm. The resulting BMF web had a basis weight of 100 g/m$^2$ and an average fiber diameter of less than about 10 micrometers.

CONTROL WEB IV

A control web of the polyurethane resin (Morthane TM PS440-200) was prepared according to the procedure of Example 1, except that only one extruder, which was maintained at 230° C., was used which was connected directly to the BMF die through a gear pump, and the die and air temperatures were maintained at 230° C. The resulting BMF web had a basis weight of 100 g/m$^2$ and an average fiber diameter of less than about 10 micrometers.

Table 3 summarizes the tensile modulus values for BMF webs comprising two-layer microfibers of varying PE/PU compositions.

TABLE 3

| Example | Tensile Modulus Two-Layer PE/PU BMF Webs 100 g/m$^2$ Basis Weight | |
|---|---|---|
| | Pump Ratio (parts PE/PU) | MD Tensile Modulus (kPa) |
| Control III | 100:0 | 1172 |
| 8 | 75:25 | 4923 |
| 9 | 50:50 | 3737 |
| 10 | 25:75 | 2654 |
| Control IV | 0:100 | 2130 |

EXAMPLE 11

A BMF web having a basis weight of 50 g/m$^2$ and comprising five-layer microfibers having an average diameter of less than about 10 micrometers was prepared according to the procedure of Example 1, except that a poly(ethylene terephthalate) resin (PET having an I.V.=0.60 and a melting point of about 257° C., prepared as described in U.S. Pat. No. 4,939,008, col. 2, line 6 to col. 3, line 20) was substituted for the polypropylene and a poly(esterurethane) (PU) resin (Morthane TM PS 440-200, available from Morton Thiokol Corp.) was substituted for the Morthane TM PS 455-200 (in a 75:25 ratio), the melt streams were delivered to the five-layer feedblock at about 280° C. and about 230° C., respectively, and the feedblock, die and air temperatures were maintained at 280° C., 280° C. and 270° C., respectively.

EXAMPLE 12

A BMF web having a basis weight of 50 g/m$^2$ and comprising five-layer microfibers having an average diameter of less than about 10 micrometers was prepared according to the procedure of Example 11, except that the PET and PU melt streams were delivered to the five-layer feedblock in a 50:50 ratio.

EXAMPLE 13

A BMF web having a basis weight of 50 g/m$^2$ and comprising five-layer microfibers having an average diameter of less than about 10 micrometers was prepared according to the procedure of Example 11, except that the PET and PU melt streams were delivered to the five-layer feedblock in a 25:75 ratio.

CONTROL WEB V

A control web of the poly(ethylene terephthalate) (I.V.=0.60) resin was prepared according to the procedure of Example 1, except that only one extruder, which was maintained at about 300° C., was used which was connected directly to the BMF die through a gear pump, and the die and air temperatures were maintained at 300° C. and 305° C., respectively. The resulting BMF web had a basis weight of 100 g/m$^2$ and an average fiber diameter of less than about 10 micrometers.

Table 4 summarizes the tensile modulus values for BMF webs comprising five-layer microfibers of varying PET/PU ratios.

TABLE 4
Tensile Modulus
Five-Layer PET/PU BMF Webs
50 g/m² Basis Weight

| Example | Pump Ratio (parts PET/PU) | MD Tensile Modulus (kPa) |
|---|---|---|
| Control V | 100:0 | 772[1] |
| 11 | 75:25 | 9674 |
| 12 | 50:50 | 10770 |
| 13 | 25:75 | 12376 |
| Control IV | 0:100 | 1834 |

[1] 100 g/m² basis weight.

EXAMPLE 14

A BMF web having a basis weight of 50 g/m² and comprising five-layer microfibers having an average diameter of less than about 10 micrometers was prepared according to the procedure of Example 1, except that a 40 blend of Kraton ™ G-1657, a hydrogenated styrene/ethylene-butylene/styrene A-B-A block copolymer (SEBS) available from Shell Chemical Corp., and a linear low-density polyethylene (LLDPE) Aspun ™ 6806, 105 MI, available from Dow Chemical, was substituted for the Morthane ™ PS 455-200, the extruder temperatures were maintained at 250° C. and 270° C., respectively, the melt streams were delivered to a five-layer feedblock maintained at 270° C. at a 75:25 ratio, and the die and primary air temperatures were maintained at 270° C. and 255° C., respectively.

EXAMPLE 15

A BMF web having a basis weight of 50 g/m² and comprising five-layer microfibers having an average diameter of less than about 10 micrometers was prepared according to the procedure of Example 14, except that the PP and SEBS/LLDPE blend melt streams were delivered to the five-layer feedblock in a 50:50 ratio.

EXAMPLE 16

A BMF web having a basis weight of 50 g/m² and comprising five-layer microfibers having an average diameter of less than about 10 micrometers was prepared according to the procedure of Example 14, except that the PP and SEBS/LLDPE blend melt streams were delivered to the five-layer feedblock in a 25:75 ratio.

CONTROL WEB VI

A control web of the 60/40 SEBS/LLDPE blend was prepared according to the procedure of Example 1, except that only one extruder, which was maintained at 270° C., was used which was connected directly to the BMF die through a gear pump, and the die and air temperatures were maintained at 270° C. The resulting BMF web had a basis weight of 50 g/m² and an average fiber diameter of less than about 10 micrometers.

Table 5 summarizes the tensile modulus values for BMF webs comprising five-layer microfibers of varying PP//SEBS/LLDPE ratios.

TABLE 5
Tensile Modulus
Five-Layer PP//SEBS/LLDPE BMF Webs
50 g/m² Basis Weight

| Example | Pump Ratio (parts PP/Blend) | MD Tensile Modulus (kPa) |
|---|---|---|
| Control I | 100:0 | 2034 |
| 14 | 75:25 | 18685 |
| 15 | 50:50 | 12011 |
| 16 | 25:75 | 6978 |
| Control VI | 0:100 | 434 |

EXAMPLE 17

A BMF web having a basis weight of 50 g/m² and comprising two-layer microfibers having an average diameter of less than about 10 micrometers was prepared according to the procedure of Example 14, except that a two-layer feedblock assembly was substituted for the five-layer feedblock.

EXAMPLE 18

A BMF web having a basis weight of 50 g/m² and comprising two-layer microfibers having an average diameter of less than about 10 micrometers was prepared according to the procedure of Example 17, except that the PP and SEBS/LLDPE blend melt streams were delivered to the two-layer feedblock in a 50:50 ratio.

EXAMPLE 19

A BMF web having a basis weight of 50 g/m² and comprising two-layer microfibers having an average diameter of less than about 10 micrometers was prepared according to the procedure of Example 17, except that the PP and SEBS/LLDPE blend melt streams were delivered to the two-layer feedblock in a 25:75 ratio.

Table 6 summarizes the tensile modulus values for BMF webs comprising two-layer microfibers of varying PP//SEBS/LLDPE compositions.

TABLE 6
Tensile Modulus
Two-Layer PP//SEBS/LLDPE BMF Webs
50 g/m² Basis Weight

| Example | Pump Ratio PP/Blend | MD Tensile Modulus kPa |
|---|---|---|
| Control I | 100:0 | 2034 |
| 17 | 75:25 | 10197 |
| 18 | 50:50 | 7357 |
| 19 | 25:75 | 3103 |
| Control VI | 0:100 | 434 |

EXAMPLE 20

A BMF web having a basis weight of 100 g/m² and comprising two-layer microfibers having an average diameter of less than about 10 micrometers was prepared according to the procedure of Example 8, except that the collector distance was 15.2 cm (6 in.).

EXAMPLE 21

A BMF web having a basis weight of 100 g/m² and comprising two-layer microfibers having an average diameter of less than about 10 micrometers was prepared according to the procedure of Example 9, except that the collector distance was 15.2 cm (6 in.). The machine direction conformability was 101 grams, and the cross direction conformability was 162 grams.

EXAMPLE 22

A BMF web having a basis weight of 100 g/m² and comprising two-layer microfibers having an average diameter of less than about 10 micrometers was prepared according to the procedure of Example 10, except that the collector distance was 15.2 cm (6 in.). The machine direction conformability was 56 grams, and the cross direction conformability was 85 grams.

Table 7 summarizes the MD modulus values for a number of two-layer PE/PU web compositions which were prepared utilizing two collector distances.

TABLE 7

Web Modulus as a Function of Collector Distance for Various Two-Layer PE/PU Pump Ratios
100 g/m² Basis Weight

| Example | Pump Ratio PE/PU | Collector Distance (cm) | MD Tensile Modulus (kPa) |
|---|---|---|---|
| 8 | 75:25 | 30.5 | 4923 |
| 20 | 75:25 | 15.2 | 12590 |
| 9 | 50:50 | 30.5 | 3737 |
| 21 | 50:50 | 15.2 | 9494 |
| 10 | 25:75 | 30.5 | 2654 |
| 22 | 25:25 | 15.2 | 7929 |

EXAMPLE 23

A BMF web having a basis weight of 100 g/m² and comprising twenty-seven-layer microfibers having an average diameter of less than about 10 micrometers was prepared according to the procedure of Example 7, except that the PP and PU melt streams were delivered to the twenty-seven-layer feedblock such that the outer layer of the fibers was PU rather than PP (I/O vs O/I for Example 7) and the die orifices had a diameter of about 0.0017 inches versus 0.0015 inches for Example 7.

Table 8 summarizes the MD modulus for two twenty-seven-layer layer PP/PU microfiber webs where the order of polymer feed into the feedblock was reversed, thereby inverting the composition of the outer layer of the microfiber.

TABLE 8

Effect of Outside Component
Twenty-Seven-Layer 25/75 PP/PU Pump Ratio
100 g/m² Basis Weight

| Example | Layer Composition | MD Tensile Modulus (kPa) |
|---|---|---|
| 23(a) | O/I | 14390 |
| 23 | I/O | 11632 |

EXAMPLE 24

A BMF web having a basis weight of 100 g/m² and comprising twenty-seven-layer microfibers having an average diameter of less than about 10 micrometers was prepared according to the procedure of Example 7, except that the PP and PU melt streams were delivered to the twenty-seven-layer feedblock which was maintained at 250° C. in a 75/25 ratio from two extruders which were maintained at 250° C. and 210° C., respectively, and a smooth collector drum was positioned 15.2 cm from the BMF die. The PP and PU melt streams were introduced into the feedblock assembly such that the outer layer of the fiber was PP (O/I).

EXAMPLE 25

A BMF web having a basis weight of 100 g/m² and comprising twenty-seven-layer microfibers having an average diameter of less than about 10 micrometers was prepared according to the procedure of Example 24, except that the PP and PU melt streams were delivered to the twenty-seven-layer feedblock in a 50/50 ratio. The machine direction conformability was 296 grams, and the cross direction conformability was 507 grams.

EXAMPLE 26

A BMF web having a basis weight of 100 g/m² and comprising twenty-seven-layer microfibers having an average diameter of less than about 10 micrometers was prepared according to the procedure of Example 24 except that the PP and PU melt streams were delivered to the twenty-seven-layer feedblock in a 25/75 ratio.

EXAMPLE 27

Figure 4:
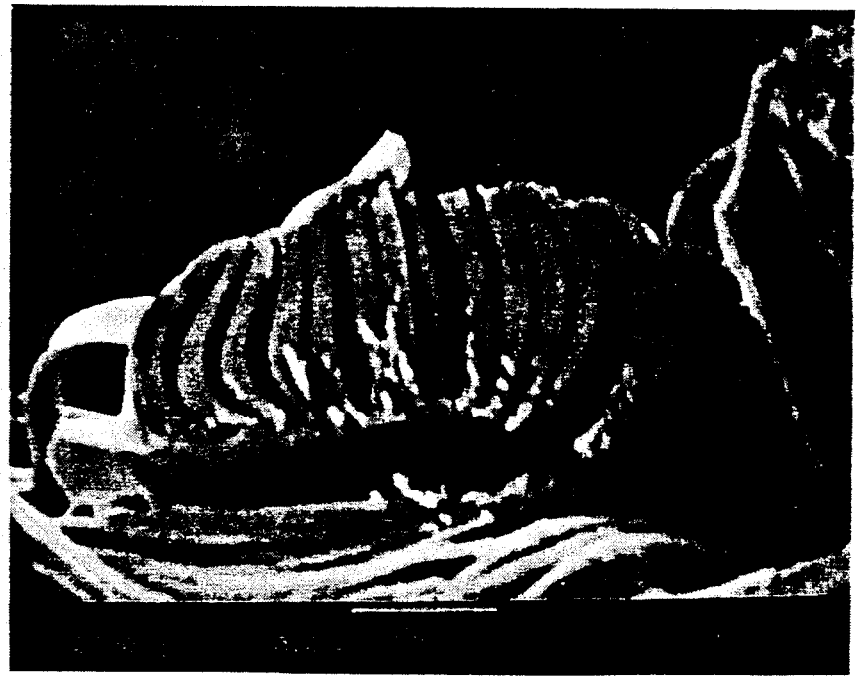

A BMF web having a basis weight of 100 g/m² and comprising twenty-seven-layer microfibers having an average diameter of less than about 10 micrometers was prepared according to the procedure of Example 24, except that a LLDPE (Aspun TM 6806, 105 MFR, available from Dow Chemical) was substituted for the PP and the PE and PU melt streams were delivered to the twenty-seven-layer feedblock which was maintained at 210° C. in a 75/25 ratio from two extruders which were both maintained at 210° C. A scanning electron micrograph (FIG. 4-2000x) of a cross section of this sample was prepared after the polyurethane was washed out with tetrahydrofuran. The sample was then cut, mounted and prepared for analysis by standard techniques.

EXAMPLE 28

A BMF web having a basis weight of 100 g/m² and comprising twenty-seven-layer microfibers having an average diameter of less than about 10 micrometers was prepared according to the procedure of Example 27, except that the PE and PU melt streams were delivered to the twenty-seven-layer feedblock in a 50/50 ratio.

EXAMPLE 29

A BMF web having a basis weight of 100 g/m² and comprising twenty-seven-layer microfibers having an average diameter of less than about 10 micrometers was prepared according to the procedure of Example 27, except that the PE and PU melt streams were delivered to the twenty-seven-layer feedblock in a 25/75 ratio.

Table 9 summarizes the MD tensile modulus for several twenty-seven-layer microfiber webs where the composition of the outer layer of the fiber varied between PP and PE.

TABLE 9

Effect of PP vs. PE on MD Web Tensile Modulus
27 Layer PP/PU and PE/PU Webs
100 g/m² Basis Weight

| Example | Web Composition Polymers | Ratio | MD Tensile Modulus (kPa) |
|---|---|---|---|
| 24 | PP/PU | 75:25 | 95940 |
| 25 | PP/PU | 50:50 | 46396 |
| 26 | PP/PU | 25:75 | 28090 |
| 27 | PE/PU | 75:25 | 19926 |

TABLE 9-continued

Effect of PP vs. PE on MD Web Tensile Modulus
27 Layer PP/PU and PE/PU Webs
100 g/m² Basis Weight

| Example | Web Composition Polymers | Ratio | MD Tensile Modulus (kPa) |
|---|---|---|---|
| 28 | PE/PU | 50:50 | 12328 |
| 29 | PE/PU | 25:75 | 7819 |

The recovery behavior of BMF webs comprising multi-layered BMF fibers was studied by subjecting samples of BMF webs consisting of various multi-layered fiber compositions to elongations of 100, 200 and 400% and monitoring the length of the samples after the elongation force had been removed and the samples allowed to relax for a period of one minute. Elastic recovery was calculated using the formula:

$$\% \text{ Elastic Recovery} = \frac{L_{Stretched} - L_{Recovered}}{L_{Stretched} - L_{Initial}} \times 100$$

Results of this study are summarized in Tables 10-15.

EXAMPLE 30

A BMF web having a basis weight of 100 g/m² and comprising three-layer microfibers having an average diameter of less than about 10 micrometers was prepared according to the procedure of Example 22, except that the PE and PU copolymer melt streams were delivered to a three-layer feedblock in a manner such that the outer layer of the fiber was PU (I/O configuration).

EXAMPLE 31

A BMF web having a basis weight of 100 g/m² and comprising three-layer microfibers having an average diameter of less than about 10 micrometers was prepared according to the procedure of Example 21, except that the PE and PU polymer melt streams were delivered to a three-layer feedblock in a manner such that the outer layer of the fiber was PU (I/O configuration).

EXAMPLE 32

A BMF web having a basis weight of 50 g/m² and comprising three-layer microfibers having an average diameter of less than about 10 micrometers was prepared according to the procedure of Example 3, except that the PP and PU melt streams were delivered to a three-layer feedblock.

EXAMPLE 33

A BMF web having a basis weight of 50 g/m² and comprising three-layer microfibers having an average diameter of less than about 10 micrometers was prepared according to the procedure of Example 2 except, that the PP and PU melt streams were delivered to a three-layer feedblock.

EXAMPLE 34

A BMF web having a basis weight of 75 g/m² and comprising three-layer microfibers having an average diameter of less than about 10 micrometers was prepared according to the procedure of Example 3.

EXAMPLE 35

A BMF web having a basis weight of 155 g/m² and comprising three-layer microfibers having an average diameter of less than about 10 micrometers was prepared according to the procedure of Example 3.

EXAMPLE 36

A BMF web having a basis weight of 100 g/m, and comprising three-layer microfibers having an average diameter of less than about 10 micrometers was prepared according to the procedure of Example 3, except that Pellathane TM 2103-80WC, a poly(etherurethane) available from Dow Chemical Corp. was substituted for the Morthane TM PS 455-200, the extruders delivering the PP and PU melts were maintained at 240° C. and 210° C., respectively, the PP and PU melt streams were delivered to a three-layer feedblock, which was maintained at 240° C., and the die and air temperatures were maintained at 230° C. and 215° C., respectively.

EXAMPLE 37

A BMF web having a basis weight of 190 g/m² and comprising three-layer microfibers having an average diameter of less than about 10 micrometers was prepared according to the procedure of Example 36.

EXAMPLE 38

A BMF web having a basis weight of 100 g/m² and comprising five-layer microfibers having an average diameter of less than about 10 micrometers was prepared according to the procedure of Example 3, except that Pellathane TM 2103-80WC, a poly(etherurethane) available from Dow Chemical Corp. was substituted for the Morthane TM PS 455-200, the extruders delivering the PP and PU melts were maintained at 240° C. and 210° C., respectively, the PP and PU melt streams were delivered to a five-layer feedblock, which was maintained at 240° C., and the die and air temperatures were maintained at 230° C. and 220° C., respectively.

CONTROL WEB VII

A control web of the poly(etherurethane) resin (Pellathane TM 2103-80WC) was prepared according to the procedure of Example 1, except that only one extruder, which was maintained at 210° C., was used which was connected directly to the BMF die through a gear pump and the die and air temperatures were maintained at 210° C. The resulting BMF web had a basis weight of 100 g/m² and an average fiber diameter of less than about 10 micrometers.

EXAMPLE 39

A BMF web having a basis weight of 100 g/m² and comprising five-layer microfibers having an average diameter of less than about 10 micrometers was prepared according to the procedure of Example 1, except that Kraton TM G-1657, (SEBS) was substituted for the Morthane TM PS 455-200, both extruder temperatures were maintained at 260° C., the melt streams were delivered to a five-layer feedblock maintained at 240° C. at a 62.5:37.5 ratio, and the die and primary air temperatures maintained at 240° C. and 275° C., respectively.

EXAMPLE 40

A BMF web having a basis weight of 100 g/m² and comprising five-layer microfibers having an average diameter of less than about 10 micrometers was prepared according to the procedure of Example 39, except that PP and SEBS melt streams were delivered to the feedblock in a 25:75 ratio.

EXAMPLE 41

A BMF web having a basis weight of 100 g/m² and comprising two layer microfibers having an average diameter of less than about 10 micrometers was prepared according to the procedure of Example 1 except that a poly(esterurethane) (PU) resin (Morthane PS 440-200, available from Morton Thiokol Corp.) was substituted for the Morthane PS 455-200, the second extruder was maintained at 230° C., and the PP and PU melt streams were delivered to the two layer feed block in a 50:50 ratio.

EXAMPLE b 42

A BMF web having a basis weight of 100 g/m² and comprising two layer microfibers having an average diameter of less than about 10 micrometers was prepared according to the procedure of Example 1 except that a poly(esterurethane) (PU) resin (Morthane PS 440-200, available from Morton Thiokol Corp.) was substituted for the Morthane PS 455-200, the second extruder was maintained at 230° C., and the PP and PU melt streams were delivered to the two layer feed block in a 25:75 ratio.

TABLE 10

Recovery Behavior
Multi-Layered 25:75 PP/PU BMF Webs
100 g/m² Basis Weight

| Example | # of Layers | Initial Length (mm) | Post Elongation Length (mm) | Recovered Length (mm) |
|---|---|---|---|---|
| 4 | 2 | 25.4 | 51 | 33.5 |
| 4 | 2 | 25.4 | 76 | 38.8 |
| 4 | 2 | 25.4 | 127 | 48.6 |
| 5 | 3 | 25.4 | 51 | 37.3 |
| 5 | 3 | 25.4 | 76 | 52.5 |
| 5 | 3 | 25.4 | 127 | 86.5 |
| 6 | 5 | 25.4 | 51 | 39.6 |
| 6 | 5 | 25.4 | 76 | 56.8 |
| 6 | 5 | 25.4 | 127 | 95.1 |
| 7 | 27 | 25.4 | 51 | 37.8 |
| 7 | 27 | 25.4 | 76 | 53.5 |
| 7 | 27 | 25.4 | 127 | 92.6 |

TABLE 11

Elastic Recovery
Multi-Layered 25:75 PP/PU BMF Webs
100 g/m² Basis Weight

| | # of | % Recovery After Elongation of | | |
| Example | Layers | 100% | 200% | 400% |
|---|---|---|---|---|
| 4 | 2 | 68 | 74 | 77 |
| 5 | 3 | 54 | 46 | 40 |
| 6 | 5 | 45 | 38 | 31 |
| 7 | 27 | 52 | 45 | 34 |

TABLE 12

Recovery Behavior
Multi-Layered PE/PU BMF Webs
100 g/m² Basis Weight

| Example | Ratio/ # of Layers | Initial Length (mm) | Post Elongation Length (mm) | Recovered Length (mm) |
|---|---|---|---|---|
| 22 | (25:75) 2 | 25.4 | 51 | 29.5 |
|  |  | 25.4 | 76 | 34 |

TABLE 12-continued

Recovery Behavior
Multi-Layered PE/PU BMF Webs
100 g/m² Basis Weight

| Example | Ratio/ # of Layers | Initial Length (mm) | Post Elongation Length (mm) | Recovered Length (mm) |
|---|---|---|---|---|
|  |  | 25.4 | 127 | 45 |
| 21 | (50:50) 2 | 25.4 | 51 | 32.3 |
|  |  | 25.4 | 76 | 39.3 |
|  |  | 25.4 | 127 | 47.6 |
| 30 | (25:75) 3 | 25.4 | 51 | 31 |
|  |  | 25.4 | 76 | 39.1 |
|  |  | 25.4 | 127 | 63.3 |
| 31 | (50:50) 3 | 25.4 | 51 | 33 |
|  |  | 25.4 | 76 | 45.3 |
|  |  | 25.4 | 127 | 68.5 |

TABLE 13

Elastic Recovery
Multi-Layered PE/PU BMF Webs
100 g/m² Basis Weight

| | # of | % Recovery After Elongation of | | |
| Example | Layers | 100% | 200% | 400% |
|---|---|---|---|---|
| 22 | 2 | 84 | 83 | 81 |
| 21 | 2 | 73 | 73 | 78 |
| 30 | 3 | 78 | 73 | 63 |
| 31 | 3 | 70 | 61 | 58 |

TABLE 14

Recovery Behavior
PP vs PE Two-Layer BMF
100 g/m² Basis Weight

| Example | Poly/Ratio of Layers | Initial Length (mm) | Post Elongation Length (mm) | Recovered Length (mm) |
|---|---|---|---|---|
| 42 | (PP/PU) 25:75 | 25.4 | 51 | 30.9 |
|  |  | 25.4 | 76 | 34.8 |
| 41 | (PP/PU) 50:50 | 25.4 | 51 | 32.3 |
|  |  | 25.4 | 76 | 37.6 |
| 22 | (PE/PU) 25:75 | 25.4 | 51 | 29.0 |
|  |  | 25.4 | 76 | 33.1 |
| 21 | (PE/PU) 50:50 | 25.4 | 51 | 30.8 |
|  |  | 25.4 | 76 | 36.5 |

TABLE 15

Elastic Recovery
PP vs PE In Two-Layer BMF
100 g/m² Basis Weight

| | Comp of | % Recovery After Elongation of | | |
| Example | Layers | 100% | 200% | 400% |
|---|---|---|---|---|
| 42 | PP/PU | 79 | 81 | —* |
| 41 | PP/PU | 73 | 76 | —* |
| 22 | PE/PU | 86 | 85 | —* |
| 21 | PE/PU | 79 | 78 | —* |

*Sample broke on attempting to stretch to 400% elongation.

In addition to monitoring the web recovery under ambient conditions, samples of several webs were subjected to post elongation annealing at elevated temperatures to determine if further recovery would be realized at elevated temperatures. Unless indicated otherwise, the web samples were placed in a circulating air oven at the indicated temperature for a period of 0.5 minutes, and the samples measured to determine if further recovery had occurred Results of these studies are summarized in Tables 16–18.

TABLE 16

Elastic Recovery Properties of Polypropylene/Polyurethane (455-200) Elongated/Annealed Webs

| Example | Comp. Polymer/ Ratio | # Layers | Basis Wt. (g/m₂) | Init. Length (mm) | Elong. Length (mm) | Rc'vd. Length (mm) | Sample Orient. | Ann. Temp. (°C.) | Pre Ann. Length (mm) | Post Ann. Length (mm) |
|---|---|---|---|---|---|---|---|---|---|---|
| 32 | PP/PU 25/75 | 3 | 50 | 26.9 | 79.7 | 49.3 | XMD | 90 | 43.1[1] | 33.2 |
| 33 | PP/PU 50/50 | 3 | 50 | 26.9 | 79.7 | 53.3 | XMD | 90 | 48.1[1] | 35.2 |
| 3 | PP/PU 25/75 | 5 | 50 | 26.9 | 79.7 | 57.7 | XMD | 90 | 53.4[1] | 43.2 |
| 2 | PP/PU 50/50 | 5 | 50 | 26.9 | 79.7 | 61.2 | XMD | 90 | 56.2[1] | 50.2 |
| 32 | PP/PU 25/75 | 3 | 50 | 26.6 | 53.0 | 36.0 | XMD | 125 | 34.5[1] | 31.1 |
| 33 | PP/PU 25/75 | 3 | 50 | 26.7 | 79.7 | 49.3 | XMD | 125 | 45.2[1] | 33.8 |
| 33 | PP/PU 50/50 | 3 | 50 | 26.6 | 53.0 | 39.1 | XMD | 125 | 36.1[1] | 32.1 |
| 33 | PP/PU 50/50 | 3 | 50 | 26.7 | 79.7 | 53.8 | XMD | 125 | 47.3[1] | 35.2 |
| 3 | PP/PU 25/75 | 5 | 50 | 26.6 | 53.0 | 39.0 | XMD | 125 | 37.0[1] | 33.0 |
| 3 | PP/PU 25/75 | 5 | 50 | 26.7 | 79.7 | 57.9 | XMD | 125 | 53.9[1] | 42.7 |
| 2 | PP/PU 50/50 | 5 | 50 | 26.6 | 53.0 | 42.0 | XMD | 125 | 39.0[1] | 36.0 |
| 2 | PP/PU 50/50 | 5 | 50 | 26.7 | 79.7 | 63.3 | XMD | 125 | 53.2[1] | 49.2 |
| Cntl II | PU | — | 50 | 25.4 | 125 | 30.5 | MD | 90 | 30.5 | 26.8 |
| Cntl I | PP | — | 50 | 25.4[2] | — | — | MD | — | — | — |
| 32 | PP/PU 25/75 | 3 | 50 | 26.5 | 79.8 | 51.2 | MD | 90 | 51.2 | 33.5 |
| 32 | PP/PU 25/75 | 3 | 50 | 27.0 | 133.0 | 64.2 | MD | 90 | 64.2 | 36.8 |
| 33 | PP/PU 50/50 | 3 | 50 | 26.5 | 79.8 | 54.1 | MD | 90 | 54.1 | 34.4 |
| 33 | PP/PU 50/50 | 3 | 50 | 27.0 | 133.0 | 77.1 | MD | 90 | 77.1 | 52.3 |
| 3 | PP/PU 25/75 | 5 | 50 | 26.5 | 79.8 | 57.0 | MD | 90 | 57.0 | 42.2 |
| 3 | PP/PU 25/75 | 5 | 50 | 27.0 | 133.0 | 88.4 | MD | 90 | 88.4 | 56.3 |
| 2 | PP/PU 50/50 | 5 | 50 | 26.5 | 79.8 | 63.4 | MD | 90 | 63.4 | 50.3 |
| 2 | PP/PU 50/50 | 5 | 50 | 27.0 | 133.0 | 100.0 | MD | 90 | 100.0 | 77.2 |
| 34 | PP/PU 25/75 | 5 | 75 | 26.5 | 79.8 | 50.3 | MD | 90 | 50.3 | 36.8 |
| 34 | PP/PU 25/75 | 5 | 75 | 27.0 | 133.0 | 87.5 | MD | 90 | 87.5 | 52.5 |
| 6 | PP/PU 25/75 | 5 | 100 | 26.5 | 79.8 | 53.4 | MD | 90 | 53.4 | 39.4 |
| 6 | PP/PU 25/75 | 5 | 100 | 27.0 | 133.0 | 80.0 | MD | 90 | 80.0 | 47.7 |
| 34 | PP/PU 25/75 | 5 | 155 | 26.5 | 79.8 | 54.3 | MD | 90 | 54.3 | 39.4 |
| 34 | PP/PU 25/75 | 5 | 155 | 27.0 | 133.0 | 80.0 | MD | 90 | 80.0 | 47.7 |

[1] A delay of 24 hrs. between measuring the initial recovery length and the annealing experiment allowed further relaxation of the BMF web and additional recovery to occur.
[2] Polypropylene BMF was inelastic and broke on attempted elongation.

TABLE 17

Elastic Recovery Properties of Polypropylene/Polyurethane (Pellathane 2103-80WC) Elongated/Annealed Webs

| Example | Comp. Polymer/ Ratio | # Layers | Basis Wt. (g/m₂) | Init. Length (mm) | Elong. Length (mm) | Rc'vd. Length (mm) | Sample Orient. | Ann. Temp. (°C.) | Pre Ann. Length (mm) | Post Ann. Length (mm) |
|---|---|---|---|---|---|---|---|---|---|---|
| 36 | PP/PU 25/75 | 3 | 100 | 26.9 | 79.7 | 42.7 | XMD | 90 | 39.2[1] | 37.1 |
| 37 | PP/PU 25/75 | 3 | 190 | 26.9 | 79.7 | 44.8 | XMD | 90 | 39.7[1] | 37.1 |
| 36 | PP/PU 25/75 | 3 | 100 | 26.6 | 53.0 | 34.1 | XMD | 125 | 31.1[1] | 30.1 |
| 36 | PP/PU 25/75 | 3 | 100 | 26.7 | 79.7 | 41.2 | XMD | 125 | 32.8[1] | 32.3 |

TABLE 17-continued

Elastic Recovery Properties of
Polypropylene/Polyurethane (Pellathane 2103-80WC)
Elongated/Annealed Webs

| Example | Comp. Polymer/ Ratio | # Layers | Basis Wt. (g/m$_2$) | Init. Length (mm) | Elong. Length (mm) | Rc'vd. Length (mm) | Sample Orient. | Ann. Temp. (°C.) | Pre Ann. Length (mm) | Post Ann. Length (mm) |
|---|---|---|---|---|---|---|---|---|---|---|
| 37 | PP/PU 25/75 | 3 | 190 | 26.6 | 53.0 | 34.1 | XMD | 125 | 31.2[1] | 30.1 |
| 37 | PP/PU 25/75 | 3 | 190 | 26.7 | 79.7 | 42.3 | XMD | 125 | 33.1[1] | 33.1 |
| Cntl VII | PU | — | 100 | 25.4 | 125 | 34.6 | MD | 90 | 34.6 | 28.4 |
| Cntl I | PP | — | 100 | 25.4 | — | — | MD | — | — | — |
| 37 | PP/PU 25/75 | 3 | 100 | 26.5 | 79.8 | 37.9 | MD | 90 | 37.9 | 31.7 |
| 37 | PP/PU 25/75 | 3 | 100 | 27.0 | 133.0 | 46.5 | MD | 90 | 46.5 | 33.7 |
| 38 | PP/PU 25/75 | 5 | 100 | 26.5 | 79.8 | 46.2 | MD | 90 | 46.2 | 37.3 |
| 38 | PP/PU 25/75 | 5 | 100 | 27.0 | 133.0 | 67.1 | MD | 90 | 67.1 | 42.3 |

[1] A delay of 24 hrs. between measuring the inital recovery length and the annealing experiment allowed further relaxation of the BMF web and additional recovery to occur.
[2] Polypropylene BMF was inelastic and broke on attempted elongation.

TABLE 18

Elastic Recovery Properties of
Polypropylene/Kraton (G-1657)
Elongated/Annealed Webs

| Example | Comp. Polymer/ Ratio | # Layers | Basis Wt. (g/m$_2$) | Init. Length (mm) | Elong. Length (mm) | Rc'vd. Length (mm) | Sample Orient. | Ann. Temp. (°C.) | Pre Ann. Length (mm) | Post Ann. Length (mm) |
|---|---|---|---|---|---|---|---|---|---|---|
| 39 | PP/Kraton 37.5/62.5 | 5 | 100 | 26.5 | 79.8 | 51.2 | MD | 90 | 51.2 | 43.2 |
| 39 | PP/Kraton 37.5/62.5 | 5 | 100 | 27.0 | 133.0 | 87.3 | MD | 90 | 87.3 | 73.1 |
| 40 | PP/Kraton 25/75 | 5 | 100 | 26.5 | 79.8 | 40.4 | MD | 90 | 40.4 | 33.6 |
| 40 | PP/Kraton 25/75 | 5 | 100 | 27.0 | 133.0 | 81.5 | MD | 90 | 81.5 | 60.0 |

EXAMPLE 43

Figure 5:
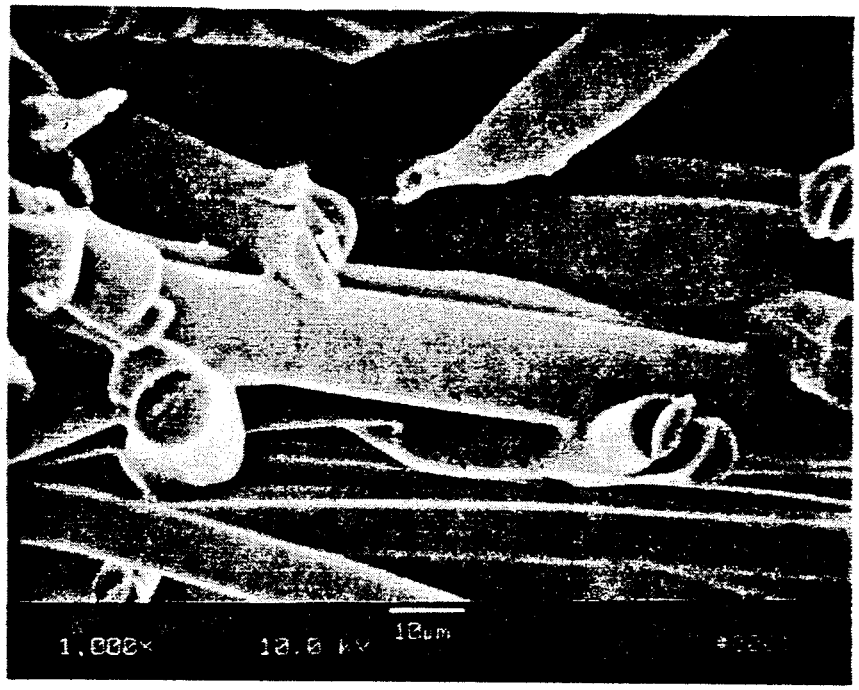
FIGS. 4 and 5 are scanning electron micrographs of web cross sections, for Examples 27 and 43, respectively, prepared by the invention method.

A BMF web was prepared according to the procedure of Example 8 except that the PE and PU melt stream were delivered to a three-layer feedblock. The samples were prepared for SEM analysis as per Example 27 except the PU was not removed, FIG. 5 (1000x).

The various modifications and alterations of this invention will be apparent to those skilled in the art without departing from the scope and spirit of this invention and this invention should not be restricted to that set forth herein for illustrative purposes.

We claim:

1. An extensible nonwoven web comprising melt-blown microfibers each of said microfibers having at least two substantially continuous layers throughout said microfiber length comprised of at least one first layer of a low modules material and at least one second layer of a relatively nonelastic higher modulus material capable of undergoing substantial permanent deformation.

2. A melt-blow nonwoven web of claim 1 wherein certain of the multi-layer microfibers are crimped, the at least one second layer or relatively nonelastic material of said crimped multi-layer microfibers being oriented.

3. A melt-blow nonwoven web of claim 1 wherein the low modulus material comprises an elastomer and the web displays asymmetrical elasticity created by stretching the extensible melt-blow web in at least one direction.

4. The melt-blow nonwoven web of claim 1 wherein the low modulus material comprises an elastomer and the web displays asymmetrical elasticity in more than one direction created by stretching the extensible web by differing degrees in said more than one direction.

5. The melt-blow nonwoven web of claim 3 wherein the web can be elastically stretched by more than 50% and recovered in its direction of elasticity.

6. The melt-blown nonwoven web of claim 3 wherein the web can be elastically stretched by less than 50% and recovered in its direction of elasticity.

7. The melt-blown nonwoven web of claim 4 wherein the web can be elastically stretched by more than 50% and recovered in its direction of elasticity.

8. The melt-blown nonwoven web of claim 1 forming a tape backing further comprising a layer of pressure sensitive adhesive on at least one face of said backing.

9. The melt-blown nonwoven web of claim 1 wherein the web has an extensibility of at least 100%.

10. The melt-blow nonwoven web of claim 1 wherein the low modulus material comprises an elastomer and the web shrinks when heated substantially above ambient conditions.

11. The melt-blown nonwoven web of claim 10 wherein the web shrinks by at least 10% when heated above about 60° C.

12. The melt-blown nonwoven web of claim 10 wherein the web shrinks by at least 30% when heated above about 90° C.

13. The melt-blown nonwoven web of claim 1 further comprising at least one adhesive layer.

14. The melt-blown nonwoven web of claim 13 wherein the web has an extensibility of at least 50%.

15. The melt-blown nonwoven web of claim 13 wherein the web has an extensibility of at least 150%.

16. The melt-blown nonwoven web of claim 8 wherein the web has pressure adhesive on two faces and the web modulus is less than 50,000 PSI.

17. The melt-blown nonwoven web of claim 1 wherein the layers are concentric.

18. The melt-blown nonwoven web of claim 1 wherein the layers are longitudinally layered.

19. The melt-blown nonwoven web of claim 17 wherein the outer sheath layer comprises a heat or sonic bondable layer with at least one internal core layer of an elastomeric material.

20. The melt-blown nonwoven web of claim 19 wherein the outer bondable layer comprises an ethylene vinyl acetate copolymer.

21. The melt-blown nonwoven web of claim 19 wherein the outer bondable layer comprises an ethylene copolymer.

22. The melt-blown nonwoven web of claim 19 wherein the outer bondable layer comprises an ethylene polymer.

23. The melt-blown nonwoven web of claim 21 wherein the inner elastomeric layer comprises a polyurethane.

24. The melt-blown nonwoven web of claim 1 wherein the average fiber diameter is less than about 10 micrometers.

25. The melt-blown nonwoven web of claim 8 wherein the web modulus is between 5,000 and 30,000 PSI.

26. The melt-blown nonwoven web of claim 18 wherein the melt-blown microfibers have 3 or more layers.

27. The melt-blown nonwoven web of claim 18 wherein the melt-blown microfibers have 5 or more layers.

28. The melt-blown nonwoven web of claim 18 wherein at least one outer layer comprises a heat or sonic bondable layer with at least one layer of an elastomeric material.

29. The melt-blown nonwoven web of claim 28 wherein the outer bondable layer comprises an ethylene polymer or copolymer.

30. The melt-blown nonwoven web of claim 28 wherein the outer bondable layer comprises an ethylene vinyl acetate copolymer.

* * * * *